United States Patent [19]

Rhein et al.

[11] Patent Number: 5,281,735

[45] Date of Patent: Jan. 25, 1994

[54] DISILANOATES OF DISILACYCLOHEXADIENES

[75] Inventors: Robert Rhein; James C. Baldwin, both of Ridgecrest, Calif.

[73] Assignee: The United States of America as represented by the Secretary of the Navy, Washington, D.C.

[21] Appl. No.: 94,665

[22] Filed: Jul. 20, 1993

[51] Int. Cl.$^5$ .............................................. C07F 7/08
[52] U.S. Cl. .................................................. 556/406
[58] Field of Search ........................................ 556/406

[56] References Cited

U.S. PATENT DOCUMENTS 2,160,915  6/1939  Schreiber ........................... 556/406
3,456,018  8/1969  Atwell ............................... 260/448.2
4,937,364  6/1990  Okinoshima ......................... 556/406

OTHER PUBLICATIONS

Watanabe et al., The Journal of Organometallic Chemistry 128(1977) 173-175.

Primary Examiner—Paul F. Shaver
Attorney, Agent, or Firm—Stuart H. Nissim; Melvin J. Sliwka; John L. Forrest, Jr.

[57] ABSTRACT

A commercially viable method of making disilacyclohexadiene polymers with unsurpassed thermal stability is made possible by using the dialkali metal salt of the diol of disilacyclohexadiene as the starting material for polymerization. The structure of the new alkali metal compound and a method of preparing it are disclosed. Uses for the new compound are also described.

21 Claims, No Drawings

DISILANOATES OF DISILACYCLOHEXADIENES

BACKGROUND OF THE INVENTION

1. Field of Invention

This invention pertains to a composition of matter and a method of preparing it. More precisely, this invention involves the chemistry of organo-silicon compounds and a new compound of this class. Specifically, this invention reveals the compound 1,4-dimethyl-1,4-disilacyclohexadiene-1,4-di(alkali metal silanoate) and a method of making it. This compound is useful as a starting material in the manufacture of silicon containing polymers, which are particularly well suited for use in high temperature applications such as insulators, adhesives, potting agents, and composite materials.

2. Description of the Related Art

The silicone rubber industry is based on a chemical process called the direct process, wherein methyl chloride is reacted with elemental silicon to produce mixed methylchlorosilanes. The monosilicon methylchlorosilanes are then used to produce conventional silicone rubbers. The direct process produces a byproduct known as direct process residue which consists of methylchlorosilanes having multiple silicon atoms. These higher methylchlorosilanes can be processed chemically to monosilanes to increase the yield of the direct process, or they can be used as the starting material to make other organosilicon compounds.

The fraction of direct process residue that boils in the range 150°–160° C. is a source of methylchlorodisilanes. A method for isolating 1,2-dimethyltetrachlorodisilane from this fraction and then converting it to 1,2-dimethyltetramethoxydisilane has been reported by Watanabe et al in the Journal of Organometallic Chemistry, 128 (1977) 173–175. Watanabe's technique involves two steps. The disilane fraction is first chlorinated with dry hydrogen chloride in the presence of aluminum chloride to convert the unwanted trimethyltrichlorodisilane into dimethyltetrachlorodisilane. The dimethyltetrachlorodisilane is next purified by distillation and then treated with methylorthoformate to replace the chlorine atoms with methoxy groups. The result is 1,2-dimethyltetramethoxydisilane. The 1,2-dimethyltetramethoxydisilane resulting from Watanabe's technique can be converted into 1,4-dimethyl-1,4-dimethoxy-1,4-disilacyclohexadiene by the method disclosed in Atwell's U.S. Pat. No. 3,465,018. Atwell's method consists in part of reacting a substituted tetramethoxy disilane precursor with an acetylene at elevated temperature to produce a compound with the disilacyclohexadiene ring structure. Atwell's patent claims a broad class of disilacyclohexadienes with various functional groups attached to the silicon atoms in the ring. Hydrolyzable groups are specifically claimed and multiple examples are given of these substituent groups. Hydrolyzable functional groups on the silicon atoms of the ring lend themselves to further chemical reactions, most notably polymerizations.

Example 7 in Atwell's patent shows a polymer made by exposing a dihydroxy substituted disilacyclohexadiene ring compound to acid catalyzed condensation polymerization. This is a standard polymerization technique wherein water is eliminated from two hydroxyl groups, allowing an oxygen atom to bridge together two monomer molecules. The process continues until many monomers are connected. The resulting polymer, 1,4-dimethyl-2,3,5,6-tetraphenyl- 1,4-polydisilacyclohexadienol, is the only known disilacyclohexadiene ring polymer in the prior art. This polymer is reported to have a melting point ranging from 10° C. to 320° C. Such a range of melting points indicates that the polymer is not an elastomer and that it has a very broad molecular weight distribution. Moreover, complete melting at 320° C. indicates that the thermal properties are substantially inferior to other well known polymers, including many commercial polysilanes and polysiloxanes.

Disilacyclohexadiene ring polymers must be commercially viable to be truly useful. The diphenylacetylene used in the synthesis of Atwell's ring polymer is expensive and relatively rare. The applicants therefore chose to use ordinary, inexpensive acetylene gas to synthesize the disilacyclohexadiene ring structure. The result is a ring without substituent groups at the 2,3,5,6 positions. The chemistry of this "naked ring" is different than that of a ring with bulky phenyl groups attached to it. For this reason the diol of the unsubstituted ring could not be isolated. Attempts to do so led to uncontrolled polymerization and useless gooey masses. A new approach to condensation polymerization would be needed to allow unsubstituted disilacyclohexadiene to polymerize in a controlled way.

While the diol of unsubstituted disilacyclohexadiene ring proved to be very difficult to isolate, isolating the dialkali metal salt of the diol proved to be straightforward. Moreover, the dialkali metal salt can be made without first making the diol. The dialkali metal salt was found to behave like a base in the presence of acids, forming the alkali metal-acid salt and ring diol. The ring diol thus formed immediately polymerized in a controlled manner. The use of a alkali metal salt as a polymer precursor is an unconventional technique that in this case solved an otherwise intractable problem. The process can be understood as acid-base condensation polymerization, and the dialkali metal salt of the diol of disilacyclohexadiene makes it possible.

This invention provides a starting material capable of forming disilacyclohexadiene ring polymers and elastomers with outstanding thermal stability, superior to any previously known polymer. The new compound, 1,4-dimethyl-1,4-disilacyclohexadiene-1,4-di(alkali metal silanoate), is derived from one of Atwell's compounds and is able to readily enter acid-base condensation polymerizations under acidic conditions. The new compound is made from inexpensive materials, providing the potential for commercial manufacture. Both homo and copolymers have been made and tested which utilize this starting material (See copending applications by the applicants Ser. No. 08/070,031, titled Oxodimethyldisilacyclohexadiene Homopolymers, filed May 28, 1993; and, Ser. No. 08/074,097 titled Oxodimethyldisilacyclohexadiene-Siloxane Co-polymers, filed Jun. 7, 1993).

SUMMARY OF THE INVENTION

This invention provides a new compound from which high temperature stable polymers may be economically synthesized. Starting with a byproduct of the silicone rubber industry called direct process residue, dimethyltetrachlorodisilane is isolated by chlorination with HCl and AlCl$_3$ followed by distillation. This compound is then converted to 1,2-dimethyltetramethoxydisilane by reaction with methylorthoformate. The 1,2-dimethyltetramethoxydisilane is then reacted with acetylene gas at elevated temperature to produce 1,4-dimethyl-1,4-dimethoxy-1,4-disilacyclohexadiene. This compound is then reacted with alkali metal hydroxide to create the new compound, 1,4-dimethyl-1,4-disilacyclohexadiene-1,4-di(alkali metal silanoate). This new dialkali metal disilanol salt is able to enter into acid-base condensation polymerizations to form new polymers and elastomers with unsurpassed thermal stability.

DETAILED DESCRIPTION OF EMBODIMENTS

The synthesis of 1,4-dimethyl-1,4-disilacyclohexadiene-1,4-di(alkali metal silanoate) begins with the fraction of direct process residue that boils between 150° and 152° C. This fraction is refluxed in the presence of aluminum chloride while dry hydrogen chloride is bubbled into the mixture. After the reaction is complete, the liquid is decanted and distilled with acetone. The fraction boiling between 150° and 152° C. is collected for the next step. This fraction consists of almost pure dimethyltetrachlorodisilane. Methylorthoformate is next added to the dimethyltetrachlorodisilane and allowed to react for several hours in a stirred vessel at about 70° C. Vacuum distillation of the resulting mixture gives dimethyltetramethoxydisilane in the fraction boiling at 82° C. The chemistry explained in this and the preceding paragraph was first disclosed by Watanabe et al in the Journal of Organometallic Chemistry, 128(1977) 173-175.

The dimethyltetramethoxydisilane is next reacted with acetylene in the method disclosed by Atwell in U.S. Pat. No. 3,465,018. Nitrogen gas carries acetylene gas into a glass tube heated to 400° C. Into this gas stream, dimethyltetramethoxydisilane is added dropwise. The liquid reaction product is collected in a condenser equipped flask at the discharge end of the glass tube. The liquid product is then purified by vacuum distillation at less than 1 torr absolute pressure and 50° C. The resulting product is 1,4-dimethyl-1,4-dimethoxy-1,4-disilacyclohexadiene with some impurities.

The impure 1,4-dimethyl-1,4-dimethoxy-1,4-disilacyclohexadiene is next reacted with an alkali metal hydroxide dissolved in an alcohol/water solvent solution by slowly adding the silane to the alkali metal hydroxide solution. The alkali metal hydroxide solution can have a concentration from about 2 molar upto about 14 molar. Preferred alkali metal hydroxides include KOH and NAOH. The ratio of alcohol to water in the solvent is not critical, ranging from 0% upto 100% water by volume. Any alcohol can be used, preferably methanol, ethanol, isopropanol, or any mixture thereof. Ratio of alkali metal hydroxide to 1,4-dimethyl-1,4-dimethoxy-1,4-disilacyclohexadiene can be from about 2 to 1 to about 5 to 1.

The solution is then filtered and vacuum dried to remove most of the solvent. An aprotic polar solvent, for example tetrahydrofuran, DMSO, and DMF, preferably tetrahydrofuran, is then added causing a precipitate to form. The precipitate is next filtered and washed with an aprotic polar solvent and an ether, preferably THF and diethyl ether. The precipitate is then recrystallized from an alcohol, preferably isopropanol. A final wash of the solids with an alcohol and a non-polar hydrocarbon solvent, preferably isopropanol and pentane respectively, gives pure 1,4-dimethyl-1,4-disilacyclohexadiene-1,4-di(alkali metal silanoate), which is the desired product. This compound will dissolve in water, but will not chemically react with it; it is not hydrolyzable.

The preferred embodiment of this invention may be further understood by referring to the following example. This example is given to illustrate but not limit this invention.

EXAMPLE 1

Step 1

Preparation of dimethyltetrachlorodisilane from direct process residue:

Direct process residue was distilled to obtain the fraction that boils between 150° and 152° C. 754.0 grams of this fraction was refluxed in the presence of 54.9 grams of aluminum chloride, while dry HCl gas was bubbled into the mixture. After refluxing for 34 hours and 12 minutes, the mixture was cooled and the liquid decanted into another vessel where 50 ml of reagent grade acetone was added. This mixture was distilled, and 652.5 grams of the fraction boiling in the range of 150° to 152° C. was collected. Gas chromatography showed the fraction to be 97% pure. Boiling point, infrared spectroscopy, and proton NMR were used to positively identify this fraction as 1,2-dimethyl-1,1,2,2-tetrachlorodisilane.

Step 2

Preparation of dimethyltetramethoxydisilane from 1,2-dimethyl-1,1,2,2-tetrachlorodisilane:

In a stirred vessel at 68° C., 572.8 grams of methylorthoformate were added slowly to 466.0 grams of 1,2-dimethyl-1,1,2,2-tetrachlorodisilane. The mixture remained at 68° C. for 14 hours and 21 minutes. The mixture was then vacuum distilled at 28 torr, and 246.0 grams of the fraction boiling at 84° C. was collected. Gas chromatography showed the fraction to be 97% pure. Boiling point, infrared spectroscopy and proton NMR were used to positively identify this fraction as 1,2-dimethyl-1,1,2,2-tetramethoxydisilane.

Step 3

Preparation of 1,4-dimethyl-1,4-dimethoxy-1,4-disilacyclohexadiene from 1,2-dimethyl-1,1,2,2-tetramethoxydisilane and acetylene:

A pyrex tube 22 mm in diameter and 19 inches in length was heated to between 400° and 425° C. Nitrogen gas flowing at less than 10 ml/min was mixed with 43 ml/min of acetylene gas and admitted into one end of the tube. 1,2-dimethyl-1,1,2,2-tetramethoxydisilane was added dropwise at a rate of 0.142 ml/min to the inlet gas stream. Liquid reaction product was collected at the tube discharge in a condenser equipped receiving flask. Gas chromatography indicated that the liquid product had two main constituents. One was identified by boiling point and peak retention time as methyltrimethoxysilane. Boiling point, infrared spectroscopy and proton NMR were used to positively identify the other constituent as 1,4-dimethyl-1,4- dimethoxy-1,4-disilacyclohexadiene.

Excess heat during distillation of the product caused polymerization in the still. Partial purification was achieved by vacuum distillation at less than one torr absolute pressure and at temperatures below 50° C. This procedure provided 1,4-dimethyl-1,4-dimethoxy-1,4-disilacyclohexadiene of 67% purity as shown by gas chromatography.

Step 4

Preparation of 1,4-dimethyl-1,4-disilacyclohexadiene-1,4-di(potassium silanoate) from 1,4-dimethyl-1,4-dimethoxy-1,4-disilacyclohexadiene:

16 ml of crude 1,4-dimethyl-1,4-dimethoxy-1,4-disilacyclohexadiene from step 3 was added slowly to 83.2 ml of 3.835M KOH in 90% methanol and 10% water. The resulting mixture was filtered and the filtrate was vacuum evaporated at 60° C. to remove most of the solvent. 150 ml of tetrahydrofuran were then added, resulting in a precipitate and a two phase mixture. The precipitate was removed by filtration and washed with a small amount of tetrahydrofuran and ether. The precipitate was next dissolved in 100 ml of boiling isopropanol. Upon cooling, a crystalline mass separated from solution. The crystals were filtered and washed with 60 ml of isopropanol and 50 ml of pentane, followed by vacuum evaporation to remove residual solvent. 5.76 grams of crystals resulted. Proton NMR, infrared spectroscopy, and wet chemical techniques were used to identify the crystals as being pure 1,4-dimethyl-1,4-disilacyclohexadiene-1,4-di(potassium silanoate). Infrared absorption bands were found at: 2890/cm (w), 810/cm (sb) for Si-$CH_3$ and 1340/cm (ms), 930/cm (sb), speculated to be the silane ring band. The proton NMR was run in deuterium oxide and perdeuteroacetone, showing peaks at 0.0 ppm for Si-$CH_3$ and 6.95 ppm for —CH=. The crystals were white, opaque, and very fine, and were found to be soluble in water, methanol, and ethanol.

EXAMPLE 2

Various homopolymers and siloxane copolymers were made with 1,4-dimethyl-1,4-disilacyclohexadiene-1,4-di(potassium silanoate) using substitution condensation polymerization.

Numerous modifications and variations of the present invention are possible in light of the above teachings. It is therefore to be understood that within the scope of the appended claims the invention may be practiced otherwise than as specifically described herein.

What is claimed is:

1. The organo-silicon compound 1,4-dimethyl-1,4-disilacyclohexadiene-1,4-di([alkali metal] silanoate).

2. The compound of claim 1, wherein the alkali metal is selected from the group consisting of Na and K.

3. A method for preparing the compound of claim 1, comprising the steps of:
   A) dissolving alkali metal hydroxide in a solvent comprising a mixture of polar organic solvent and inorganic solvent;
   B) slowly adding crude 1,4-dimethyl-1,4-dimethoxy-1,4-disilacyclohexadiene to said alkali metal hydroxide solution;
   C) filtering the mixture from step B and vacuum evaporating the solvent;
   D) adding an aprotic polar solvent to the remaining filtrate from step C;
   E) filtering and washing the precipitate resulting from step D;
   F) recrystallizing the precipitate resulting from step E from a solvent; and,
   G) filtering, washing, and vacuum drying the crystals resulting from step F.

4. The method of claim 3 wherein the alkali metal hydroxide of step A is selected from the group consisting of KOH and NAOH.

5. The method of claim 3 wherein the polar organic solvent of step A is selected from the group consisting of methanol, ethanol, propanol, or any mixture thereof.

6. The method of claim 3 wherein the inorganic solvent of step A is water.

7. The method of claim 3 wherein the mixture of polar organic solvent and inorganic solvent of step A consists of any proportion of the two types of solvents.

8. The method of claim 3 wherein the concentration of the alkali metal hydroxide is from about 2 molar to about 14 molar.

9. The method of claim 3 wherein the dissolved alkali metal hydroxide of step A is 3.835 molar in concentration.

10. The method of claim 3 wherein the purity of the crude 1,4-dimethyl-1,4-dimethoxy-1,4-disilacyclohexadiene of step B is between 1% and 100%.

11. The method of claim 3 wherein the aprotic polar solvent of step D is tetrahydrofuran.

12. The method of claim 3 wherein the washing of the precipitate in step E is performed at least once with at least one solvent selected from the group consisting of aprotic solvents and ethers.

13. The method of claim 3 wherein the washing of the precipitate in step E is performed once with tetrahydrofuran and then once with diethyl ether.

14. The method of claim 3 wherein the solvent of step F is allowed to cool from the boiling point at atmospheric pressure to affect crystallization.

15. The method of claim 3 wherein the solvent of step F is an alcohol.

16. The method of claim 3 wherein the solvent of step F is isopropanol.

17. The method of claim 3 wherein the washing of step G is performed at least once.

18. The method of claim 3 wherein the washing of step G is performed at least twice, once with an alcohol and once with a nonpolar hydrocarbon solvent.

19. The method of claim 18 wherein the alcohol is the same alcohol used in step F.

20. The method of claim 18 wherein the alcohol is isopropanol and the nonpolar solvent is pentane.

21. The organo-silicon polymer precursor illustrated by the formula:

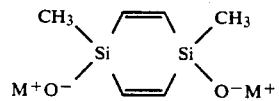

wherein M is an alkali metal; wherein the compound consists of the cis-stereoisomer (as illustrated), the trans-stereoisomer, or combinations thereof.

* * * * *